United States Patent
Gerstel

Patent Number: 5,702,671
Date of Patent: Dec. 30, 1997

[54] GAS CHROMATOGRAPHY TRANSFER LINE

[76] Inventor: Eberhard Gerstel, Aktienstr. 232-234, D-45473 Mülheim, Germany

[21] Appl. No.: 664,310

[22] Filed: Jun. 11, 1996

[30] Foreign Application Priority Data

Jun. 12, 1995 [DE] Germany ............ 195 20 715.7

[51] Int. Cl.$^6$ .................................. G01N 30/16
[52] U.S. Cl. .............. 422/103; 73/23.42; 73/863.11; 73/864.81; 96/105; 138/142; 138/143; 219/544; 219/548; 392/379; 422/89
[58] Field of Search .................. 96/105, 106, 102; 73/23.39, 23.41, 23.42, 863.11, 864.81, 864.84, 864.85, 864.86, 864.87; 422/89, 103; 219/553, 552, 544, 545, 548; 392/379; 138/32, 35, 140, 142, 143, 144, 148

[56] References Cited

U.S. PATENT DOCUMENTS

| | | | |
|---|---|---|---|
| 4,422,860 | 12/1983 | Feinstein | 96/105 |
| 4,644,140 | 2/1987 | Hillinger | 219/535 |
| 4,650,964 | 3/1987 | Vincent | 219/301 |
| 4,766,760 | 8/1988 | Poshemansky et al. | 73/23.1 |
| 5,544,276 | 8/1996 | Loux et al. | 392/480 |

FOREIGN PATENT DOCUMENTS 34 48 091  7/1985  Germany.

*Primary Examiner*—Jan Ludlow
*Attorney, Agent, or Firm*—Flehr Hohbach Test Albritton & Herbert LLP; Steven F. Caserza

[57] ABSTRACT

The invention relates to a gas chromatography transfer line, having a glass tube (12), a steel tube (13) enclosing this glass tube and a heating coil (17) enclosing the steel tube, in which a tube (15) made of a material with high thermal conductivity is arranged between the steel tube (13) and the heating coil (17), the tube (15) being provided with a series of bores (16) in the axial and in the circumferential direction and being soldered to the heating coil (17) and to the steel tube (13), the solder (20) filling the bores (16) and intermediate spaces between the steel tube (13) and the tube (15).

10 Claims, 3 Drawing Sheets

GAS CHROMATOGRAPHY TRANSFER LINE

INTRODUCTION

1. Technical Field

The invention relates to a gas chromatography transfer line which may be used in connection with a sampling head of a gas chromatographic system for transferring components of an applied sample to the analyzing part of the system.

2. Background

German Patent 34 48 091 discloses a cold sampling system for capillary gas chromatography, in which a precolumn is provided, connected to an applicator head and comprising an evaporator robe from which substances in an injected sample are transferred to a capillary column and which is enclosed by a metal tube with the formation of an annular gap used for selective rejection, this metal tube in turn being enclosed by a heating coil. In practice, only stainless steel is a suitable material for the metal tube, but this material has relatively poor thermal conductivity. For this reason, it is, on the one hand, difficult to obtain a maximum uniform temperature profile at least in the region of the precolumn where the chromatographic separation takes place and, on the other hand, to carry out heating to a desired temperature at a sufficiently high rate.

SUMMARY

An objection of the invention is therefore to provide a gas chromatography transfer line which permits fast and uniform heating or holding of a predetermined temperature virtually over its entire length.

BRIEF DESCRIPTION OF THE DRAWINGS

The invention will be explained in more detail below with the aid of an illustrative embodiment represented in the appended drawings.

DESCRIPTION OF SPECIFIC EMBODIMENTS

Figure 1:
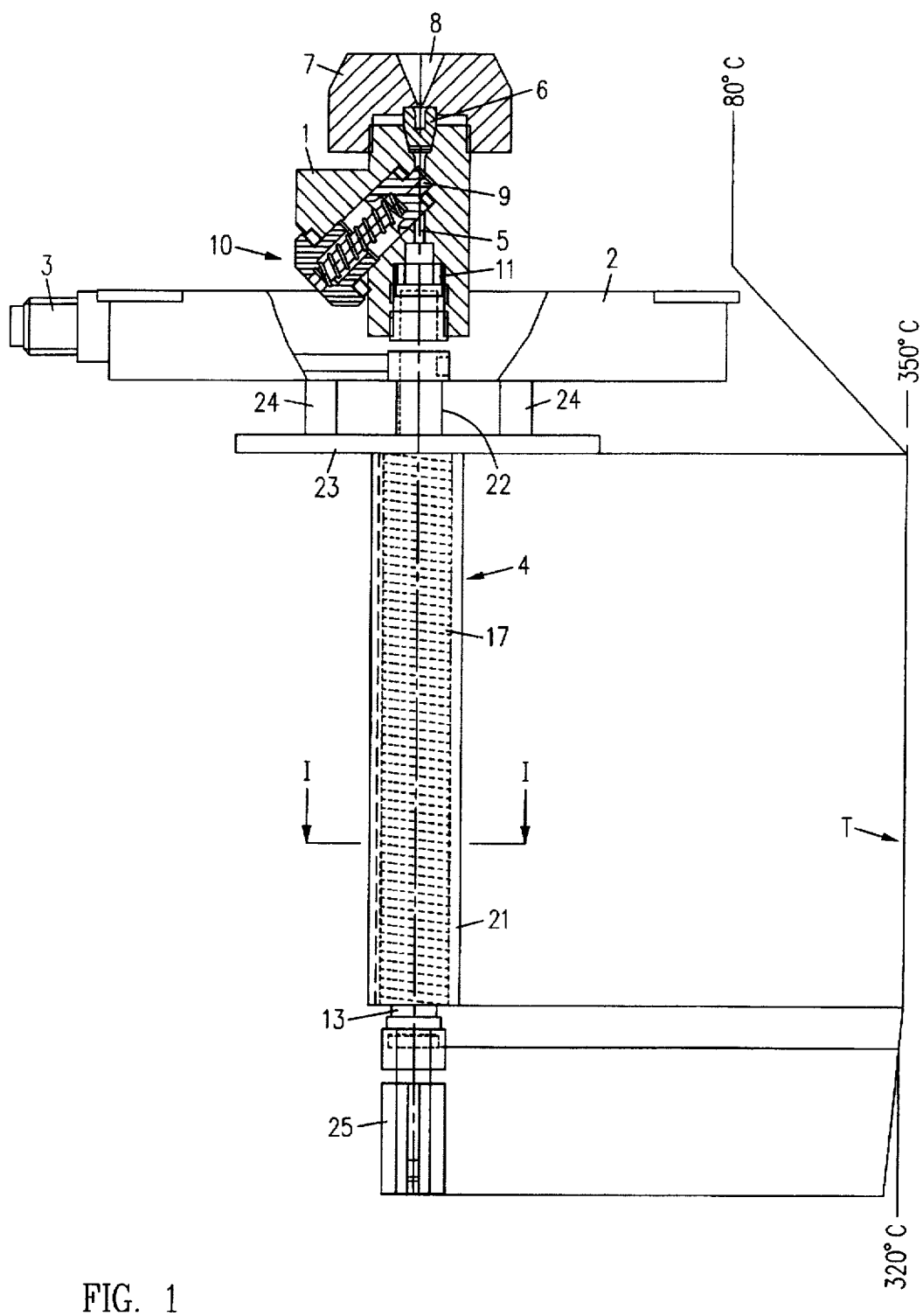
FIG. 1 somewhat schematically shows a cold sampling device for a gas chromatograph, partly in section.
Figure 2:
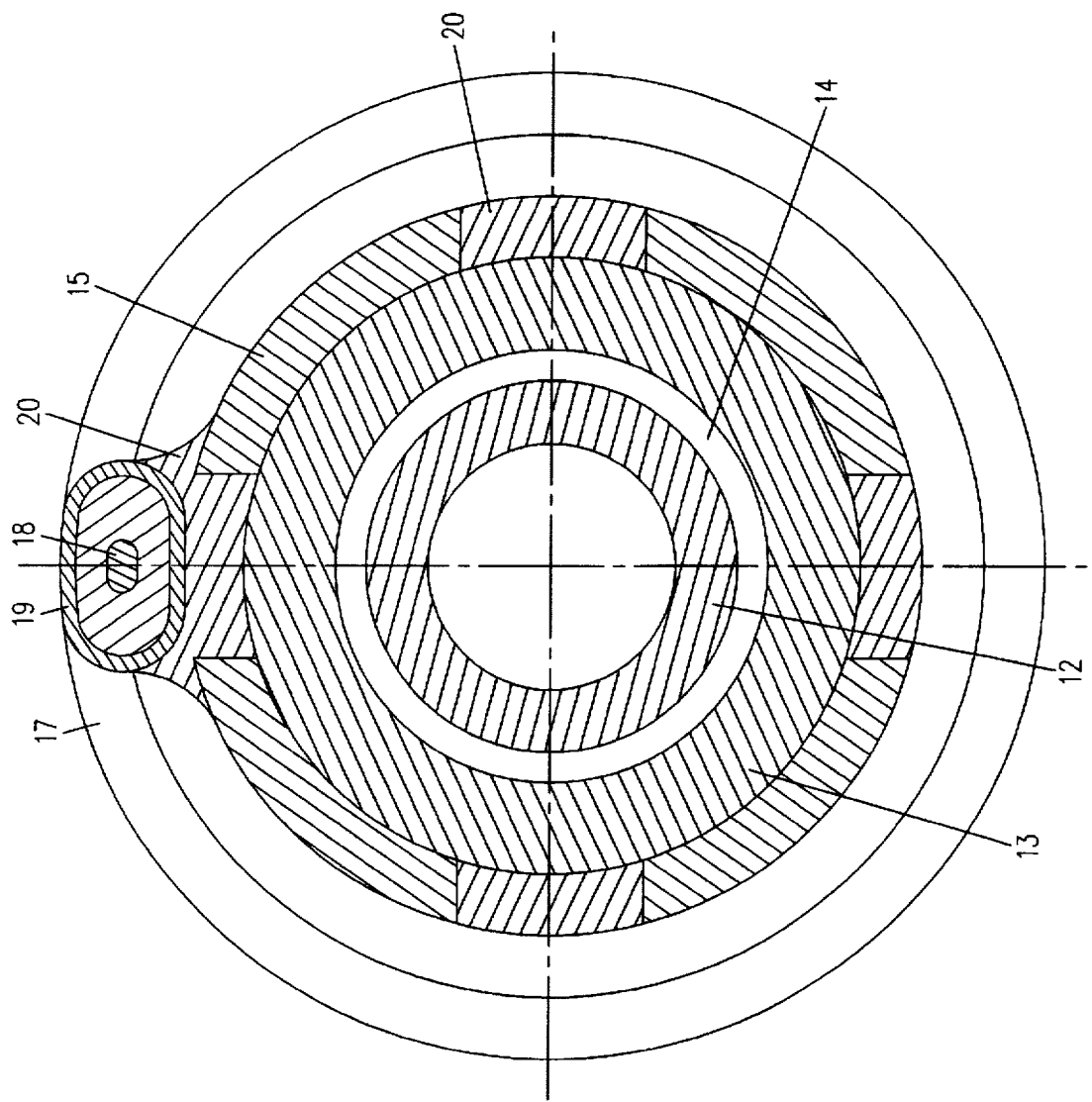
FIG. 2 shows a section along the line I—I in FIG. 1.

The cold sampling device which is represented comprises a sampling head which is provided with a carrier gas connection (not represented) and is arranged on a place-shaped support 2 which is provided with an outlet line 3. The sampling head 1 is connected to a precolumn 4 which represents a transfer line between the sampling head 1 and a capillary column (not represented) of a gas chromatograph.

The sampling head 1 comprises a bore 5 which receives a seal 6 in a widened part at the entry side, this seal furthermore being received by a cap 7 which has an insertion guide 8 for an injection needle (not represented) for sampling. When it is inserted into the bore 5, the injection needle comes into contact with a valve body 9 of a valve 10, presses the latter out of the region of the bore 5, against the action of its pretensioned spring, and thus enters the precolumn 4 which is located in the exit-side widened part of the bore 5, sealed off by means of a graphite seal 11.

The precolumn 4 comprises an inner glass tube 12, for example partly filled with glass wool or provided with a liner, into which the injection needle can be inserted, in which the sampling then takes place and into which the capillary column can be fitted on the exit side.

The gas tube 12 is arranged in a steel tube 13 made of stainless steel, an annular gap 14 being arranged between the two. The annular gap 14 is connected to the outlet line 3 and is used for selectively rejecting solvents or other chromatogram parts. This effect is achieved in that, with the outlet line 3 open, when access to the capillary column is closed at the end of the precolumn 4 remote from the applicator head 1, the carrier gas flowing past a sample which has been applied flows back to the outlet line 3 through the annular gap 14 and is thereby rejected.

Figure 3:
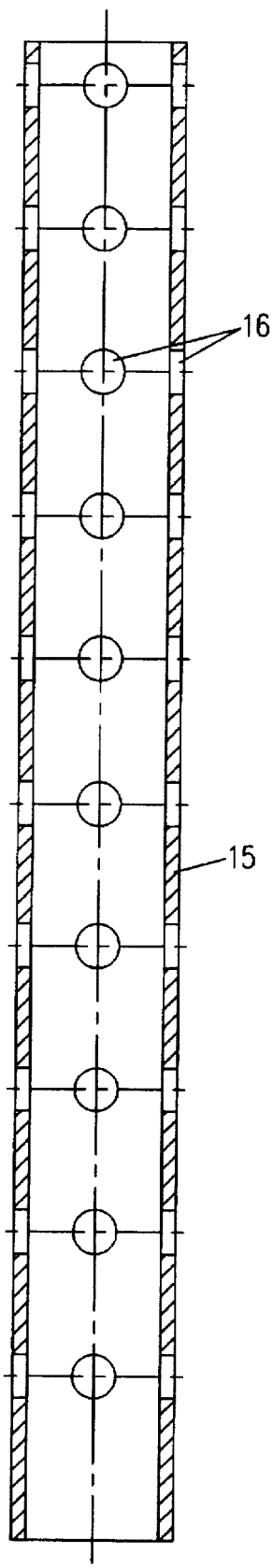
FIG. 3 shows a detail of the device in FIG. 1.

The steel tube 13 with lower thermal conductivity is enclosed by a tube 15 made of a material, such as copper, brass, silver or else gold, which has very high thermal conductivity. As can be seen from FIG. 3, the tube 15 is provided over its length, at regular distances, with a series of bores 16 which are additionally uniformly distributed in the circumferential direction. A heating coil 17, consisting of a heating conductor 18 which is enclosed inside a metallic casing tube 19 by a thermally conductive and electrically insulating material such as magnesium oxide powder, is wound onto the tube 15 and is connected to the latter by soldering. The solder 20 used for the soldering, for example copper and in particular silver solder, in this case also fills the bores 16 and the intermediate space (which remains after fitting and is not represented) between the steel tube 13 and the tube 15, so as to produce an integral body with high and uniform heat flow from the heating coil 17 to the steel tube 13.

The heating coil 17 is externally enclosed by a protective tube 21, in particular made of stainless steel, which protects a temperature sensor (not represented) which is soldered on next to the heating conductor 18 when the precolumn 4 is cryogenically cooled.

Because of the thermal dissipation which takes place there, the heating coil 17 is more tightly wound at the ends than in the central region.

Next to the applicator-head side of the heating coil 17, the steel tube 13 is fed out from the heating coil 17 and the tube 15 in order to be connected to the sampling head 1. In this case, the steel tube 13 is designed very thin, for example with a wall thickness of a few tenths of a millimeter, in the region 22 which extends as far as the support 2, in order to permit the least possible heat flow towards the sampling head 1. This very thin region 22 of the steel tube 13 thereby serves as a thermal barrier in the direction of the sampling head 1.

The thermal barrier is important insofar as applicator heads with elastomer sealing elements, in the illustrative embodiment the seal 6 and seals on the valve 10, have the problem that the sealing elements can give out gases under excessive thermal loading and vitiate the chromatogram. For this reason, applicator heads for chromatography transfer lines should be kept as cool as possible.

In order for the steel tube 13 not to be damaged in the region 22, a relatively thin support plate 23 made of stainless steel is provided parallel to the support 2, is connected to the latter via two or more spacers 24 and has the precolumn 4 together with the protective tube 21 fastened to it. It is thereby likewise not possible for a large amount of heat to flow out at this point.

Because of the high degree of heat transfer between the healing coil 17 and the steel tube 13, an essentially constant temperature profile in the glass tube 12 can be achieved in the region of the healing conductor 17, both when the precolumn 4 is being heated and when an intended final temperature has been reached. A temperature curve T has been given by way of example in FIG. 1. From the entry side of the precolumn 4 almost as far as the exit side, a constant temperature in the interior of the glass tube 12, and above all in the region in which the precolumn separation takes place, is in this case achieved. On the exit side, the temperature can decrease again slightly without causing any significant problems. If a temperature of 350° C. is required for the pre-separation, a drop to 320° C. on the exit side can be tolerated, especially since the capillary column protrudes a small distance into the glass tube 12. Towards the sampling head 1, the temperature falls virtually linearly to 80° C., so that the sampling head remains cool. The temperature curves for different temperatures are similar to each other.

The sampling head 1 which is represented is designed for internal sampling,f or example by using an injection needle; although it is in this case represented without a septum, it may also be provided with a septum. It may also be a sampling head which is designed for external sampling, in which case the glass tube 12 is filled with the sample after it has been removed and is subsequently fitted.

A metallic adaptor 25, in particular made of a material such as silver with high thermal conductivity, may be fastened on the exit side, for example using a union nut, in order to secure the connection to a chromatographic separation device, for example the capillary column.

Other gas-chromatograph transfer lines, in which chromatographic separation does not take place but substances are merely intended, for example, to be transferred to a trap of the like, can be designed in similar fashion to the precolumn 4 in order to ensure complete transfer without additional splitting.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A gas chromatography transfer line with an entry end and an exit end, comprising:

a first tube constructed of glass;

a second tube constructed of steel enclosing said first tube;

a heating coil enclosing said second tube;

a third tube constructed of a material with a thermal conductivity higher than that of the second tube;

said third tube having an axial and a circumferential direction and being arranged between said second tube and said heating coil so as to provide interstices between said second tube and said third tube, the third tube being provided with a series of bores spaced apart in said axial and in said circumferential direction and the third tube being soldered by a solder to said heating coil and to said second tube;

wherein said solder fills said bores and said interstices between said second tube and said third tube.

2. The transfer line of claim 1, wherein said third tube is made of copper, brass, gold or silver or an alloy thereof.

3. The transfer line of claim 1, wherein the solder is a copper or silver solder.

4. The transfer line of claim 1, wherein said heating coil is wound more narrowly adjacent to said entry and exit ends than therebetween.

5. The transfer line of claim 1, wherein adjacent to said entry end said second tube protrudes from said third tube and from said heating coil and has a region with reduced wall thickness.

6. The transfer line of claim 5, wherein said region is protected against damages by protecting means.

7. The transfer line of claim 6, wherein said protecting means comprises a support plate.

8. The transfer line of claim 7, wherein a sampling head for applying a sample to the transfer line is provided, said sampling head being fastened on a support means, said support plate of said protecting means being fastened to said support means.

9. The transfer line of claim 1, wherein an outer protective tube is provided enclosing said heating coil.

10. The transfer line of claim 1, wherein a metallic adaptor means is provided at said exit end.

* * * * *